(12) United States Patent
Tamaru et al.

(10) Patent No.: US 9,931,496 B2
(45) Date of Patent: Apr. 3, 2018

(54) MICRONEEDLE ARRAY AND MICRONEEDLE ARRAY DEVICE

(71) Applicants: Takuya Tamaru, Hamamatsu (JP); Noriyuki Ogai, Hamamatsu (JP); Ryo Sugimura, Hamamatsu (JP); Isamu Nonaka, Hamamatsu (JP); Yuko Wada, Hamamatsu (JP)

(72) Inventors: Takuya Tamaru, Hamamatsu (JP); Noriyuki Ogai, Hamamatsu (JP); Ryo Sugimura, Hamamatsu (JP); Isamu Nonaka, Hamamatsu (JP); Yuko Wada, Hamamatsu (JP)

(73) Assignee: ASTI CORPORATION, Hamamatsu-Shi, Shizuoka (JP)

( * ) Notice: Subject to any disclaimer, the term of this patent is extended or adjusted under 35 U.S.C. 154(b) by 65 days.

(21) Appl. No.: 14/888,074

(22) PCT Filed: May 2, 2013

(86) PCT No.: PCT/JP2013/062756
§ 371 (c)(1),
(2) Date: Oct. 29, 2015

(87) PCT Pub. No.: WO2014/178140
PCT Pub. Date: Nov. 6, 2014

(65) Prior Publication Data
US 2016/0082239 A1    Mar. 24, 2016

(51) Int. Cl.
*A61M 37/00* (2006.01)

(52) U.S. Cl.
CPC ... *A61M 37/0015* (2013.01); *A61M 2037/003* (2013.01); *A61M 2037/0023* (2013.01)

(58) Field of Classification Search
CPC ...... A61M 37/0015; A61M 2037/0023; A61M 2037/003; A61M 5/158; A61M 5/1585;
(Continued)

(56) References Cited

U.S. PATENT DOCUMENTS

| 8,790,314 B2 * | 7/2014 | Casey | A61M 5/422 604/192 |
| 2008/0091226 A1 * | 4/2008 | Yeshurun | A61B 10/0045 606/186 |

(Continued)

FOREIGN PATENT DOCUMENTS

| JP | S 56-95058 A | 8/1981 |
| JP | 2008-296037 A | 12/2008 |

(Continued)

OTHER PUBLICATIONS

Tamaru et al; English Translation of JP2012-157406 "Microneedle, microneedle array, and microneedle array device"; saved from ESpaceNet on Aug. 1, 2017.*

(Continued)

*Primary Examiner* — Laura Bouchelle
*Assistant Examiner* — Tasnim M Ahmed
(74) *Attorney, Agent, or Firm* — McGinn I.P. Law Group, PLLC.

(57) ABSTRACT

A microneedle array includes a microneedle unit that includes microneedles; and a microneedle unit support member that includes an opening, guides both ends of the microneedle unit through inclined grooves, and arranges tips of the microneedles so as to project through the opening in an inclined manner.

14 Claims, 20 Drawing Sheets

(58) Field of Classification Search
CPC .. A61M 5/3295; A61M 5/3298; A61M 5/427; A61M 2005/1586; A61M 5/32; A61M 2037/0038; A61M 2037/0061; A61B 5/150977; A61B 5/150984; A61K 9/0021
See application file for complete search history.

(56) References Cited

U.S. PATENT DOCUMENTS

| | | | |
|---|---|---|---|
| 2008/0269687 A1* | 10/2008 | Chong | A61L 15/58 604/180 |
| 2009/0216215 A1* | 8/2009 | Thalmann | A61M 5/158 604/506 |
| 2010/0121271 A1* | 5/2010 | Perriere | A61M 5/14248 604/110 |
| 2012/0041412 A1* | 2/2012 | Roth | A61M 25/10 604/500 |
| 2013/0218084 A1* | 8/2013 | Tamaru | A61M 37/0015 604/173 |
| 2016/0354591 A1* | 12/2016 | Ueno | A61M 37/0015 |

FOREIGN PATENT DOCUMENTS

| | | | | |
|---|---|---|---|---|
| JP | 2012-095736 A | 5/2012 | | |
| JP | 2012-157406 A | 8/2012 | | |
| WO | WO 2008134580 A2 * | 11/2008 | | A61M 5/422 |
| WO | WO 2012/057270 A1 | 5/2012 | | |

OTHER PUBLICATIONS

International Search Report (ISR) (PCT Form PCT/ISA/210), in PCT/JP2013/062756, dated Jul. 30, 2013.

\* cited by examiner before puncture (a)

(b)

(c)

(d)

RELATED ART

MICRONEEDLE ARRAY AND MICRONEEDLE ARRAY DEVICE

TECHNICAL FIELD

The present invention relates to a microneedle array incorporating, for example, a plurality of microneedles, and a microneedle array device using such a microneedle array, and more specifically, relates to those in which the microneedles are mounted in an inclined state with an angle against a surface, so that, during injection with the microneedles, a pain of a patient can be relieved, and leakage of a liquid medicine can be prevented.

BACKGROUND ART

Microneedle arrays provided with a plurality of microneedles are manufactured, for example, by a method to which a manufacturing process of semiconductors, such as etching, is applied. For example, Patent Document 1 discloses a method of this kind to which the manufacturing process of semiconductors is applied. The microneedle manufactured by this method is formed to be perpendicular to a flat surface (skin).

Therefore, as illustrated in FIG. 20, when a skin 203 is attempted to be pierced with a microneedle 201, since the surface of the skin 203 is deformed, the sufficient piercing cannot be performed, and as a result, a problem occurs that a liquid medicine 205 leaks out to the surface of the skin 203. In such a case, the microneedle 201 may be depressed more strongly against the skin 203 so as to be pierced, but this causes discomfort and pain to a patient.

Note that, in consideration of relieving the pain of patient during injection and effective injection of the liquid medicine 205, the preferable piercing depth of the microneedle will be around 100 to 500 µm under the skin.

In order not to cause discomfort and pain to the patient, and at the same time, in order to prevent the leakage of the liquid medicine 205 out to the surface of the skin 203, the microneedle 201 may be inclined relative to the skin 203 to perform piercing. Accordingly, the microneedle 201 can intrude into the skin 203 so as to prevent the leakage of the liquid medicine 205 out to the skin 203, and at the same time, since the tip of the microneedle 201 reaches only the shallow portion from the surface of the skin 203, the pain of the patient can be relieved.

Note that, Patent Document 2 discloses an example in which a syringe is inclined relative to the skin surface to perform piercing. Patent Document 2 shows a micro syringe of which needle can perform piercing at the angle of 45° or more relative to the skin surface.

REFERENCE DOCUMENTS OF CONVENTIONAL ART

Patent Document(s)

Patent Document 1: Official Gazette, JP 2008-296037A.
Patent Document 2: Official Gazette, JP 1981 (Sho 56)-95058A.

SUMMARY OF THE INVENTION

Problems to be Solved by Invention

However, the above structure of the prior art has the following problems:

Namely, as described above, in order to prevent the leakage of the liquid medicine 205 out to the surface of the skin 203, and at the same time, in order to relieve the pain of the patient, the microneedle 201 may be inclined relative to the skin 203 to perform piercing, but in the case of the structure of microneedle array according to the prior art, the microneedle 201 cannot perform piercing in the inclined state relative to the skin 203.

In the light of the above problem, it is an object of the present invention to provide a microneedle array and a microneedle array device, in which, the microneedles can be pierced obliquely relative to the skin, and therefore, during injection with the microneedles, the pain of the patient can be relieved, and at the same time, the leakage of the liquid medicine can be prevented.

Means to Solve the Problem

To achieve the objects mentioned above, a microneedle array according to claim 1 is comprising: microneedle units respectively having microneedles; and a microneedle units support member provided with an opening, guiding the microneedle units via inclined grooves, and protrusively disposing tips of the microneedles in an inclined state via the opening.

Moreover, according to the microneedle array of claim 2, in the microneedle array of claim 1, the microneedle support member is provided with a liquid medicine feeding port, and also is a case provided with an opening having inclined grooves.

Moreover, according to the microneedle array of claim 3, in the microneedle array of claim 2, a needle holder is incorporated in the case, and the microneedle units are held by the needle holder in an inclined state.

Moreover, according to the microneedle array of claim 4, in the microneedle array of claim 2 or claim 3, the case is composed of a liquid medicine feeding port side case provided with a liquid medicine feeding port, and an opening side case provided with the opening.

Moreover, according to the microneedle array of claim 5, in the microneedle array of claim 4, the opening side case is provided with inclined grooves for guiding the microneedle units in the inclined state.

Moreover, according to the microneedle array of claim 6, in the microneedle array of any one of claim 3 to claim 5, the microneedle unit is provided with channel bosses, and the needle holder is provided with inclined guide holes, so that, with insertion of the channel bosses into the inclined guide holes, the microneedle unit is held in an inclined state.

Moreover, according to the microneedle array of claim 7, in the microneedle array of any one of claim 1 to claim 6, the microneedle unit comprises two divided elements, and a liquid medicine channel is formed between the two divided elements.

Moreover, a microneedle array device according to claim 8 is comprising: the microneedle array of any one of claim 1 to claim 7; and a microneedle array mounting jig placed on a skin and guiding the microneedle array in an inclined direction.

Moreover, according to the microneedle array device of claim 9, in the microneedle array device of claim 8, the microneedle array mounting jig is provided with: a jig main body provided with penetration holes for passing the microneedles of the microneedle array therethrough; and guide parts for guiding the microneedle array incorporated in the jig main body in the inclined direction, so that the microneedles are introduced to the penetration holes.

Moreover, according to the microneedle array device of claim 10, in the microneedle array device of claim 9, the surface of the jig main body is provided with an adhesion part.

Moreover, according to the microneedle array device of claim 11, in the microneedle array device of claim 9 or claim 10, the jig main body is provided with a microneedle array holder for holding the incorporated microneedle array.

Moreover, according to the microneedle array device of claim 12, in the microneedle array device of claim 11, the microneedle array holder is engaging parts provided on the side surfaces of the jig main body, and the microneedle array is held by engagement of the engaging parts with engaged parts provided on the microneedle array.

Moreover, according to the microneedle array device of claim 13, in the microneedle array device of claim 12, the engaged part is composed of a non-use-state engaged part and an in-use-state engaged part, so that the non-use-state engaged part is engaged with the engaging part of the jig main body during non-use state so as to prevent unintended puncture of the microneedles, and the in-use-state engaged part is engaged with the engaging part of the jig main body during in-use state so as to maintain the puncture state of the microneedle array.

Effect of the Invention

As discussed above, a microneedle array according to claim 1 is comprising: microneedle units respectively having microneedles; and a microneedle units support member provided with an opening, guiding the microneedle units via inclined grooves, and protrusively disposing tips of the microneedles in an inclined state via the opening. With this structure, the microneedles can needled in the inclined state against a skin, whereby a pain of a patient can be relieved, and leakage of a liquid medicine can be prevented.

Moreover, according to the microneedle array of claim 2, in the microneedle array of claim 1, the microneedle support member is provided with a liquid medicine feeding port, and also is a case provided with an opening having inclined grooves. Therefore, the microneedles can be needled in the inclined state against the skin in a simple structure, whereby the above effects can be obtained.

Moreover, according to the microneedle array of claim 3, in the microneedle array of claim 1 or claim 2, a needle holder is incorporated in the case, and the microneedle units are held by the needle holder in an inclined state. With this structure, the microneedle units can be held more surely, whereby the above effects can be obtained more surely.

Moreover, according to the microneedle array of claim 4, in the microneedle array of claim 2 or claim 3, the case is composed of a liquid medicine feeding port side case provided with a liquid medicine feeding port, and an opening side case provided with the opening. With this structure, the microneedles can be needled in the inclined state against the skin in a simple structure, whereby the above effects can be obtained. Moreover, the liquid medicine can be delivered easily from the liquid medicine feeding port side case.

Moreover, according to the microneedle array of claim 5, in the microneedle array of claim 4, the opening side case is provided with inclined grooves for guiding the microneedle units in the inclined state. With this structure, the microneedles can be guided in the inclined state, whereby the piercing of the microneedles in the inclined state against the skin can be performed more surely.

Moreover, according to the microneedle array of claim 6, in the microneedle array of any one of claim 3 to claim 5, the microneedle unit is provided with channel bosses, and the needle holder is provided with inclined guide holes, so that, with insertion of the channel bosses into the inclined guide holes, the microneedle unit is held in an inclined state. With this structure, the piercing of the microneedles in the inclined state against the skin can be performed more surely, and moreover, when the needle holder is made of, for example, elastomer or rubber material, an excellent sealing performance is obtained, whereby the leakage of liquid from insertion parts of the channel bosses or from the case can be prevented.

Moreover, according to the microneedle array of claim 7, in the microneedle array of any one of claim 1 to claim 6, the microneedle unit comprises two divided elements, and a liquid medicine channel is formed between the two divided elements. Therefore, the microneedle unit itself can be manufactured easily.

Moreover, a microneedle array device according to claim 8 is comprising: the microneedle array of any one of claim 1 to claim 7; and a microneedle array mounting jig placed on a skin and guiding the microneedle array in an inclined direction. Therefore, with using of the microneedle array mounting jig, the piercing of the microneedles in the inclined state against the skin can be performed more surely.

Moreover, according to the microneedle array device of claim 9, in the microneedle array device of claim 8, the microneedle array mounting jig is provided with: a jig main body provided with penetration holes for passing the microneedles of the microneedle array therethrough; and guide parts for guiding the microneedle array incorporated in the jig main body in the inclined direction, so that the microneedles are introduced to the penetration holes. Also with this structure, the piercing of the microneedles in the inclined state against the skin can be performed more surely.

Moreover, according to the microneedle array device of claim 10, in the microneedle array device of claim 9, the surface of the jig main body is provided with an adhesion part. With this structure, the flat surface state of the skin can be maintained, whereby the insertion of the microneedles into the skin can be performed more surely.

Moreover, according to the microneedle array device of claim 11, in the microneedle array device of claim 9 or claim 10, the jig main body is provided with a microneedle array holder for holding the incorporated microneedle array. With this structure, the above effects can be obtained more surely.

Moreover, according to the microneedle array device of claim 12, in the microneedle array device of claim 11, the microneedle array holder is engaging parts provided on the side surfaces of the jig main body, and the microneedle array is held by engagement of the engaging parts with engaged parts provided on the microneedle array. Therefore, the microneedle array can be held with a simple structure.

Moreover, according to the microneedle array device of claim 13, in the microneedle array device of claim 12, the engaged part is composed of a non-use-state engaged part and an in-use-state engaged part, so that the non-use-state engaged part is engaged with the engaging part of the jig main body during non-use state so as to prevent unintended puncture of the microneedles, and the in-use-state engaged part is engaged with the engaging part of the jig main body during in-use state so as to maintain the puncture state of the microneedle array. Therefore, during non-use state, the microneedle array can be held at a non-use position so as to prevent any unintended puncture of the microneedles, and during in-use state, the microneedle array can be held at an in-use position so as to maintain the puncture state of the microneedle array. Moreover, by adjusting the position at which the in-use-state engaged part is provided, this can be served as a stopper, whereby the puncture depth can be varied easily.

BRIEF DESCRIPTION OF DRAWINGS

FIG. 12 Views according the first embodiment of the present invention, in which: FIG. 12 (a) is a side view showing a state before puncture, in which the microneedle array is mounted on the microneedle array mounting jig; and FIG. 12 (b) is a view as seen from the arrows b-b of FIG. 12 (a).

FIG. 14 Views according to the first embodiment of the present invention, in which: FIG. 14 (a) is a plan view of an opening side case; FIG. 14 (b) is a front view of the opening side case; FIG. 14 (c) is a side view of the opening side case; and FIG. 14 (d) is a sectional view as seen from the line d-d of FIG. 14 (a).

FIG. 15 Views according to the first embodiment of the present invention, in which: FIG. 15 (a) is a plan view of a needle holder; FIG. 15 (b) is a front view of the needle holder; FIG. 15 (c) is a side view of the needle holder; and FIG. 15 (d) is a sectional view as seen from the line d-d of FIG. 15 (a).

MODE(S) FOR CARRYING OUT THE INVENTION

Figure 1:
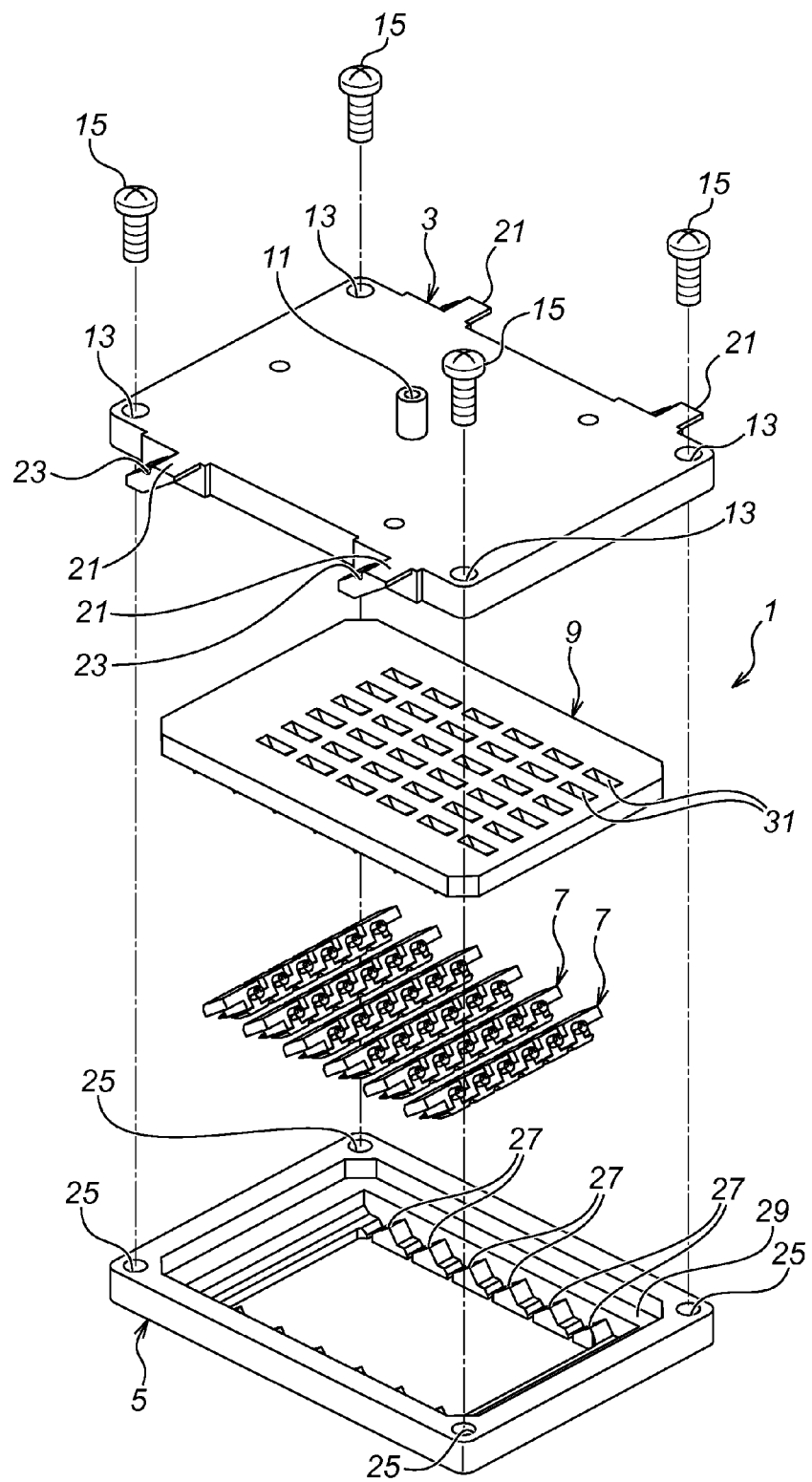
FIG. 1 An exploded perspective view of a microneedle array according to a first embodiment of the present invention.
Figure 2:
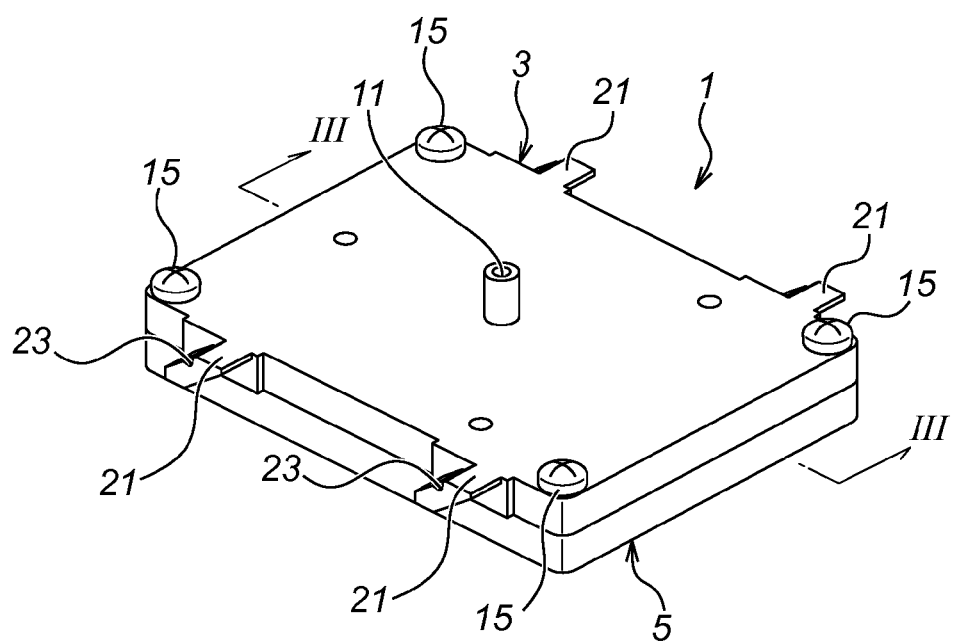
FIG. 2 A perspective view of the microneedle array according to the first embodiment of the present invention.

A first embodiment of the present invention will be explained as below, with reference to FIG. 1 to FIG. 15. FIG. 1 is an exploded perspective view of a microneedle array 1 according to the first embodiment, including a liquid medicine feeding port side case 3 and an opening side case 5. A plurality of arrays (in the present embodiment, six arrays) of microneedle units 7 is held by a needle holder 9, so as to be incorporated between the liquid medicine feeding port side case 3 and the opening side case 5.

Hereinafter, the detailed structure will be explained in order.

First, the liquid medicine feeding port side case 3 is substantially in a rectangular plate shape, with a liquid medicine feeding port 11 formed at the center thereof. Moreover, penetration holes 13 are perforated, respectively, in the four corners of the liquid medicine feeding port side case 3. Fixing screws 15 penetrate, respectively, through these four penetration holes 13.

Moreover, on the pair of side surfaces of the liquid medicine feeding port side case 3 opposing to each other, pairs of engagement projections 21, 21 are provided, respectively, in the inclined state at a predetermined angle. The pairs of the engagement projections 21, 21 have in-use-state engagement recesses 23, 23, formed therein respectively.

Note that, although only one side surface is illustrated in FIG. 1, the engagement projections 21, 21 and the in-use-state engagement recesses 23, 23 are also provided likewise, on the other side surface.

Figure 3:
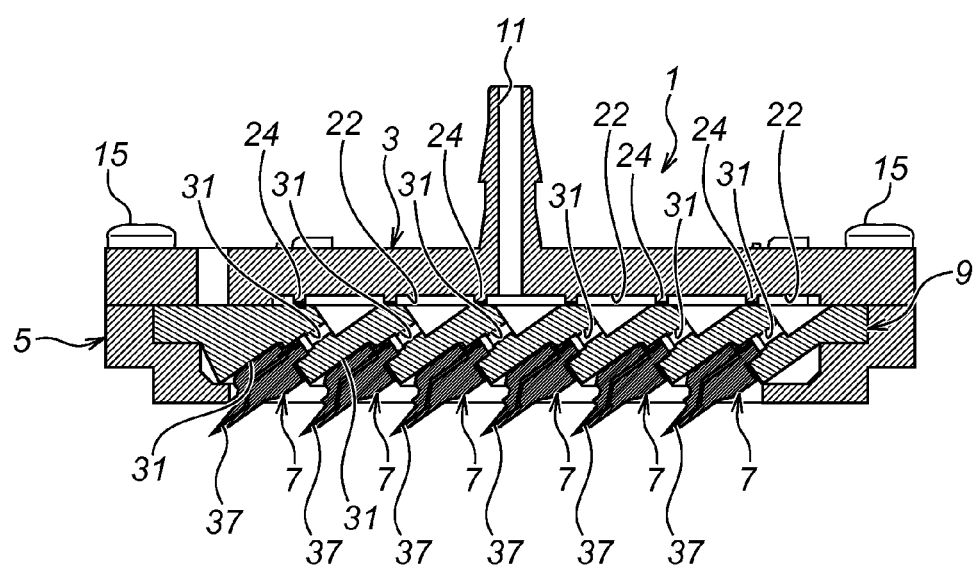
FIG. 3 A sectional view as seen from the line III-III of FIG. 2, according to the first embodiment of the present invention.

Moreover, as illustrated in FIG. 3, grate-shaped liquid medicine distribution grooves 22 are formed on the lower surface of the liquid medicine feeding port side case 3 of FIG. 3, and moreover, other parts thereon other than the liquid medicine distribution grooves 22 are formed as protrusions 24.

Figure 14:
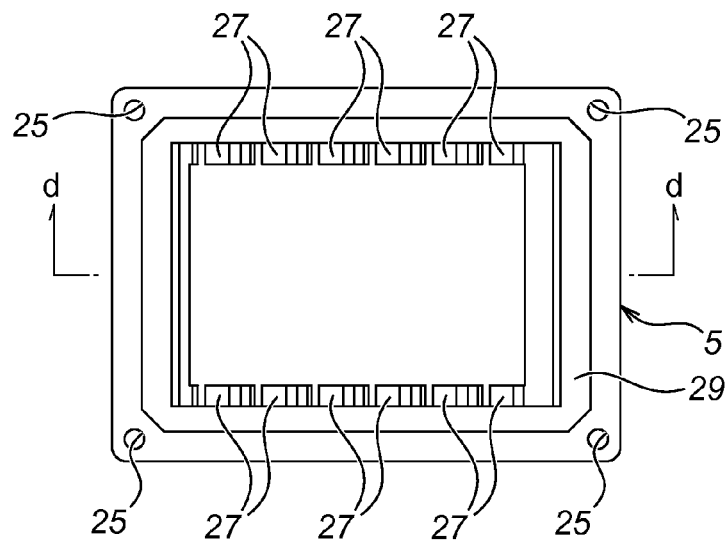
Figure 14:
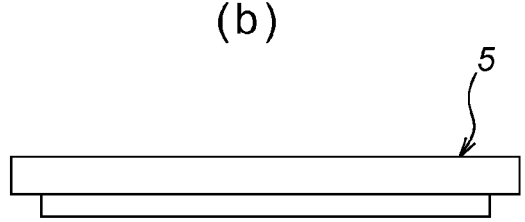
Figure 14:
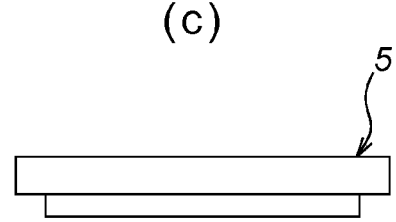
Figure 14:
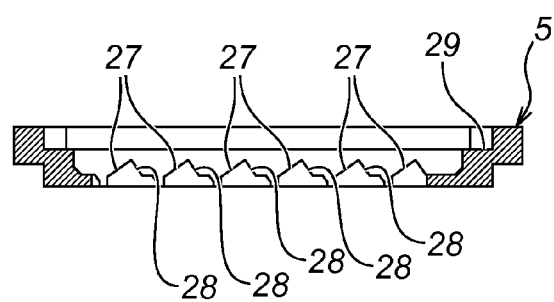

Next, the structure of the opening side case 5 is explained. As also illustrated in FIG. 14, the opening side case 5 is a hollow structure, substantially in a rectangular plate shape. Screw holes 25, 25, 25, 25 are provided, respectively, in the four corners of the opening side case 5. The fixing screws 15, 15, 15, 15, as explained above, pass through the penetration holes 13, 13, 13, 13 of the liquid medicine feeding port side case 3, and screw into the screw holes 25, 25, 25, 25, respectively. Consequently, a plurality of arrays of microneedle units 7 is incorporated and fixed between the liquid medicine feeding port side case 3 and the opening side case 5, in a state of being held by the needle holder 9.

As also illustrated in FIG. 14 (a), on the inner surfaces opposing to each other in the inside of the opening side case 5, a plurality of (in the present embodiment, six) inclined guide grooves 27, 27 is provided, respectively. With these inclined guide grooves 27, 27 disposed to be opposing to each other, the both ends of each of the microneedle units 7 are supported, and are simultaneously guided in the inclined direction. Moreover, a stopper 28 is provided in the vicinity of the inclined guide groove 27 so that, during engagement therewith, the both ends of the microneedle unit 7 become in contact with the stopper 28, whereby the position thereof is regulated.

Note that, as illustrated in FIG. 14 (b), FIG. 14 (c) and FIG. 14 (d), the portion in which the inclined guide grooves 27, 27 are formed, is in a form of protrusion in the downward direction.

Moreover, a circular stage part 29 is provided in the inner peripheral surface of the opening side case 5. The needle holder 9 is mounted on the circular stage part 29.

Figure 15:
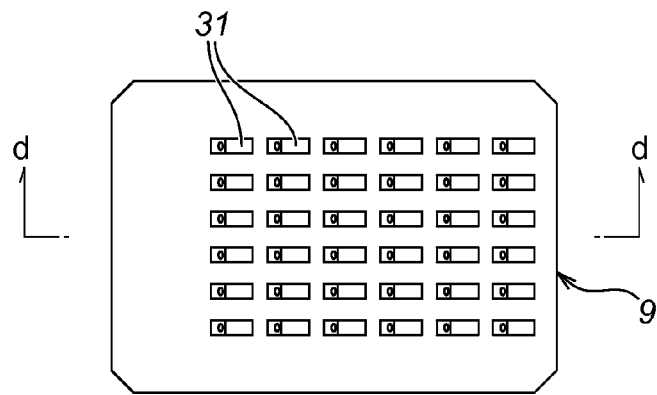
Figure 15:
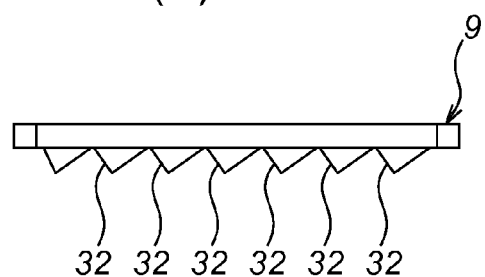
Figure 15:
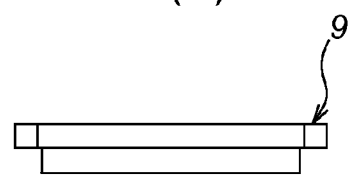
Figure 15:
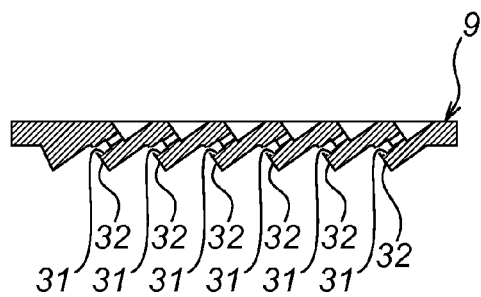
Figure 16:
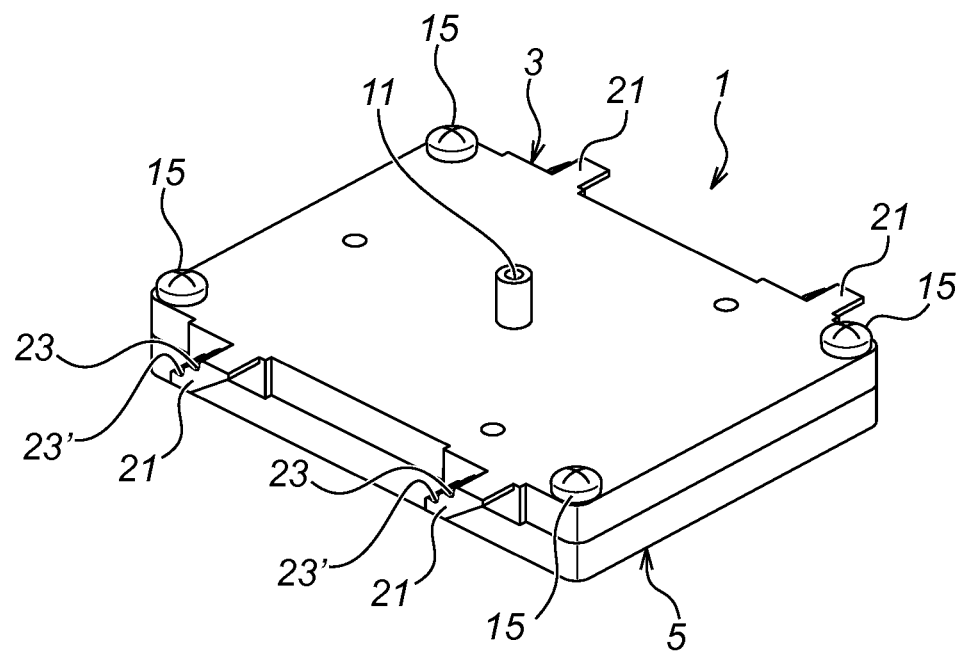
FIG. 16 A perspective view of a microneedle array according to a second embodiment of the present invention.

Next, the structure of the needle holder 9 is explained. The needle holder 9 is made of elastic body such as, for example, silicone rubber. Moreover, as illustrated in FIG. 15, the needle holder 9 is substantially in a rectangular plate shape, in which a plurality of (in the present embodiment, 6 holes×6 arrays=36 holes) inclined guide holes 31 is provided. With the plurality of inclined guide holes 31, the microneedle units 7 are held in an inclined state. Moreover, with stoppers 32 provided therewith, each of the microneedles of the microneedle unit 7 becomes in contact with the stopper 32 during engagement, whereby the position thereof is regulated. Moreover, as illustrated in FIG. 15 (b), FIG. 15 (c) and FIG. 15 (d), each portion of the inclined guide holes 31 is in a form of protrusion in the downward direction.

Note that, the inclined guide holes 31 communicate with the liquid medicine distribution grooves 22 of the liquid medicine feeding port side case 3.

Moreover, the needle holder 9 is formed to be slightly larger than the accommodated space, so as to perform the sealing function. Moreover, as illustrated in FIG. 3, with the protrusions 24 of the liquid medicine feeding port side case 3 explained above, the uplift of the needle holder 9 is prevented.

Figure 4:
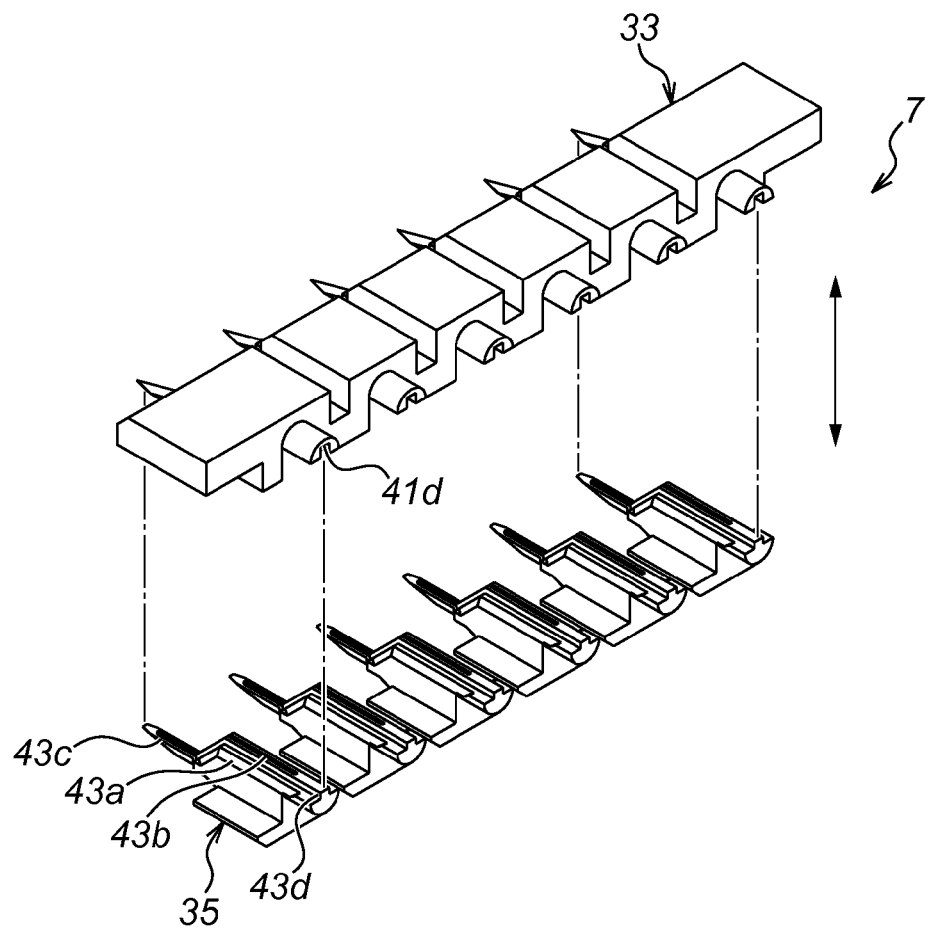
FIG. 4 An exploded perspective view of a microneedle unit used for the microneedle array, according to the first embodiment of the present invention.
Figure 5:
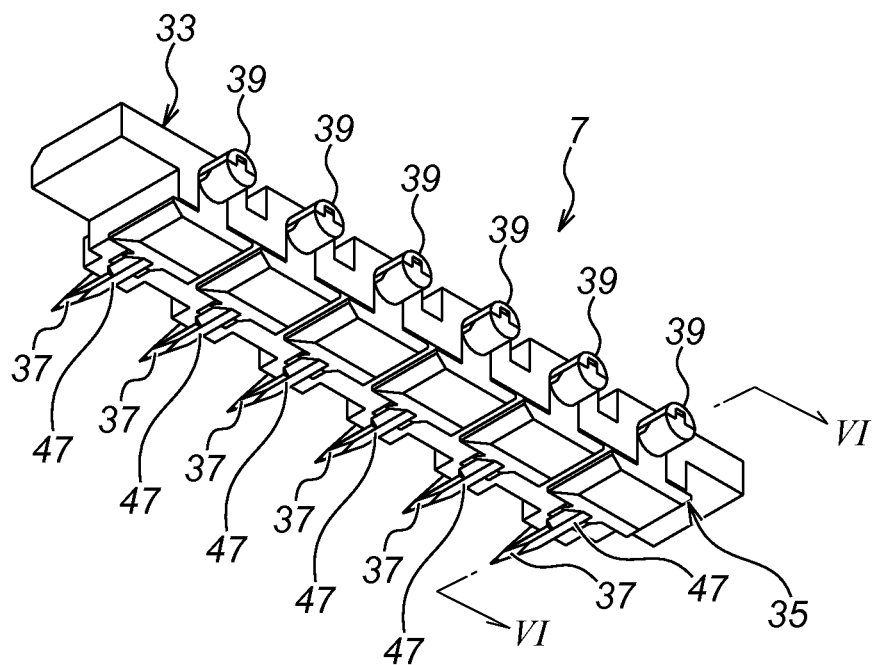
FIG. 5 A perspective view of the microneedle unit used for the microneedle array, according to the first embodiment of the present invention.

Next, the structure of the microneedle unit 7 is explained. The structure of the microneedle unit 7 is illustrated in FIG. 4 to FIG. 8. Namely, as illustrated in FIG. 4, the microneedle unit 7 is composed of two divided elements, namely a main-needle side divided element 33 and a sub-needle side divided element 35. The microneedle unit 7 is formed by bonding the main-needle side divided element 33 with the sub-needle side divided element 35. Moreover, as illustrated in FIG. 5, each of the microneedle unit 7 is provided with a plurality of (in the present embodiment, six) microneedles 37. A channel boss 39 is provided on the basement of the microneedle 37. Each of the channel bosses 39 is inserted into the inclined guide hole 31 of the needle holder 9, whereby the microneedle units 7 are held in the inclined state by the needle holder 9.

The structure of the joint surfaces between the main-needle side divided element 33 and the sub-needle side divided element 35 is explained in detail. First, a first fitting groove 41a is formed in the main-needle side divided element 33, and a second fitting groove 41b is formed at the center of the first fitting groove 41a. Moreover, a third fitting groove 41c is further formed in the tip part thereof.

On the other hand, a first fitting rib 43a in a relatively larger size is formed protrusively on the sub-needle side divided element 35.

A pair of second fitting ribs 43b, 43b is formed protrusively at the center of the first fitting rib 43a. Moreover, a third fitting rib 43c is further formed on the tip part thereof.

Thus, with the joint of the main-needle side divided element 33 with the sub-needle side divided element 35, a liquid medicine channel 45 is formed. Namely, the first fitting rib 43a is fitted with the first fitting groove 41a.

Moreover, the pair of second fitting ribs 43b, 43b is fitted with the both sides of the second fitting groove 41b. Accordingly, a part of the liquid medicine channel 45 is formed between the pair of second fitting ribs 43b, 43b. Moreover, when the third fitting rib 43c is fitted with the inside of the third fitting groove 41c, it is arranged that a gap is formed between the third fitting groove 41c and the third fitting rib 43c. This gap constitutes a remaining part of the liquid medicine channel 45.

Figure 6:
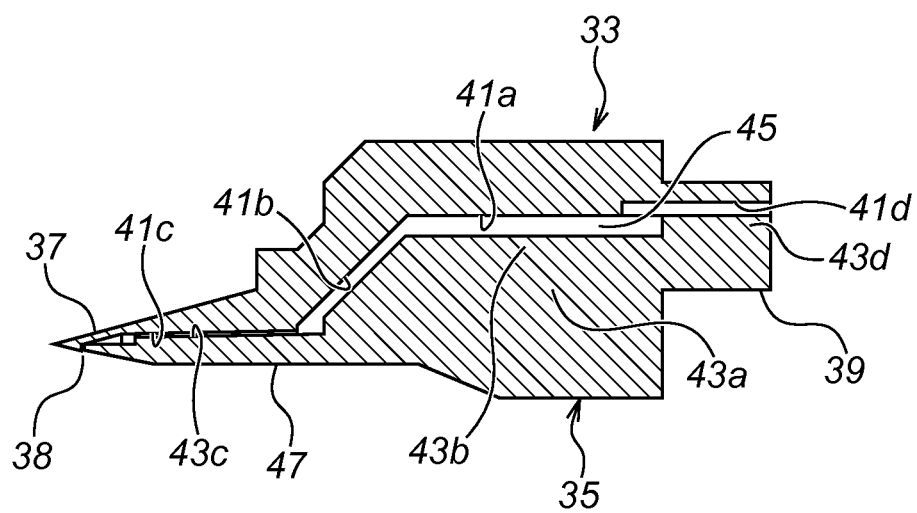
FIG. 6 A sectional view as seen from the line VI-VI of FIG. 5, according to the first embodiment of the present invention.
Figure 7:
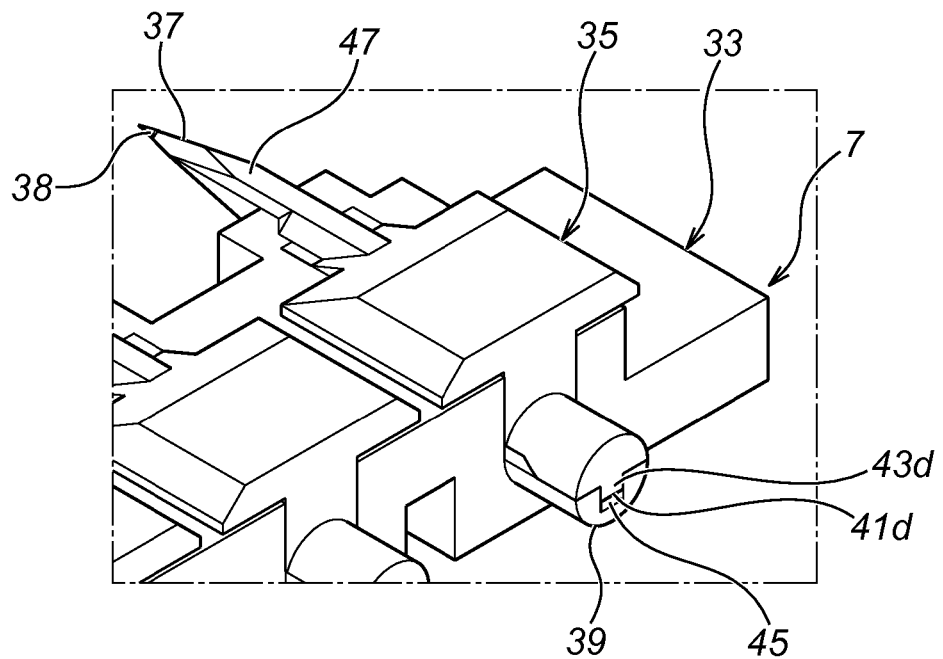
FIG. 7 A partial perspective view of the microneedle unit used for the microneedle array, according to the first embodiment of the present invention.
Figure 8:
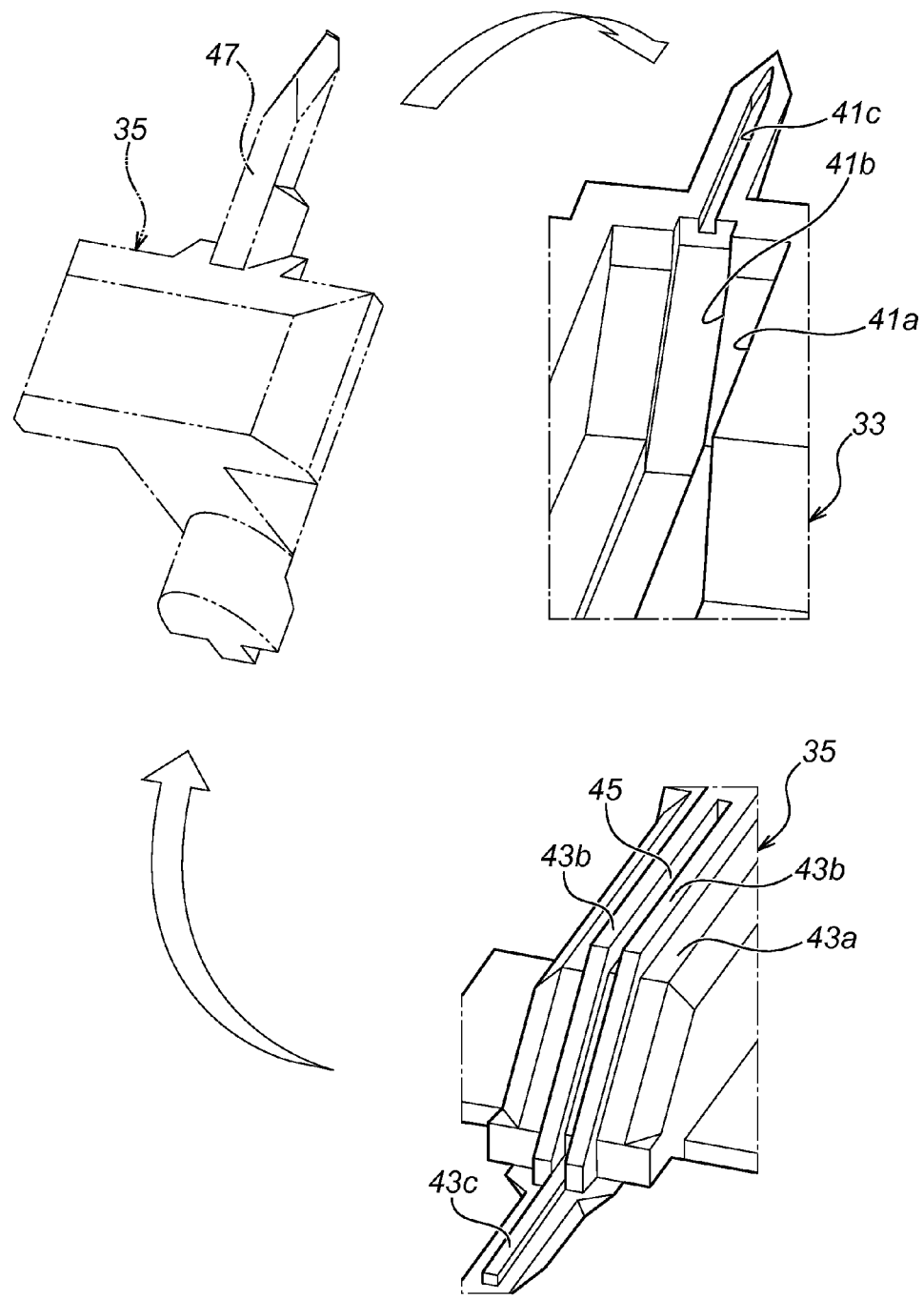
FIG. 8 Partial exploded perspective views of the microneedle unit used for the microneedle array, according to the first embodiment of the present invention.

Moreover, the rear end of the liquid medicine channel 45 extends to the portion of the channel boss 39 (as illustrated in FIG. 7). Namely, as illustrated in FIG. 6, a fourth fitting groove 41d is formed in the main-needle side divided element 33, and on the other hand, a fourth fitting rib 43d is formed on the sub-needle side divided element 35. With the fitting of the fourth fitting groove 41d with the fourth fitting rib 43d with a gap therebetween, the liquid medicine channel 45 is formed on the side of the channel boss 39.

Note that, the tip of the microneedle 37 is not adhered, so as to perform as a liquid medicine discharge port 38.

As described above, the first fitting groove 41a, the second fitting groove 41b, the third fitting groove 41c and the fourth fitting groove 41d are fitted, respectively, with the first fitting rib 43a, the pair of second fitting ribs 43b, 43b, the third fitting rib 43c and the fourth fitting rib 43d, so as to form the liquid medicine channel 45, and accordingly, the strong joint structure of the main-needle side divided element 33 with the sub-needle side divided element 35 can be obtained. Moreover, a straight part 47 is provided at the tip part of the sub-needle side divided element 35, so as to improve the puncture performance.

Note that, as for the number of microneedles 37, for example, it is preferable to provide around 10 to 1000 microneedles per 1 cm, and more preferably, around 20 to 200 microneedles.

Moreover, as for the external size of the microneedle 37, it is desirable to be thinner from the viewpoint of avoiding pains, and for example, it is preferable to be 500 μm or less. More preferably, by considering the strength, etc., of the microneedle, the size (diameter or width) may be 100 to 300 μm.

Moreover, since the puncture depth is not more than 1 mm, the length of the microneedle 37 may be around 1 mm, but by considering the deformation of the skin, etc., it is preferable to be around 1 to 2 mm.

Moreover, in the present embodiment, since the microneedles 37 are needled in the inclined state, the maximum puncture depth can be adjusted in accordance with the length of the microneedle and the angle of puncture, and therefore timely and appropriate setting can be made.

Moreover, metal or plastic may be used as the material of the microneedle 37, and from the viewpoints of mass-productivity by molding, disposability and production cost, it is preferable to use plastic, and further, from the viewpoint of safety, it is more preferable to use biodegradable resin.

Figure 9:
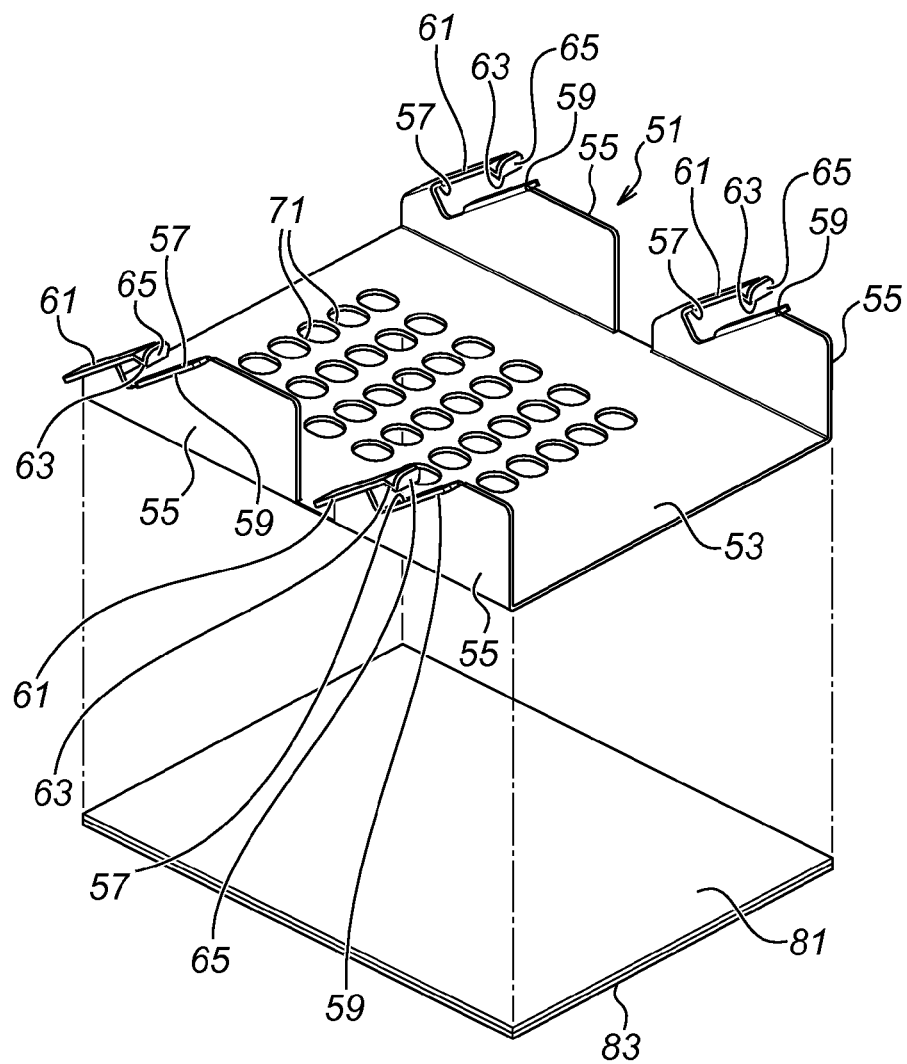
FIG. 9 A perspective view of a microneedle array mounting jig according to the first embodiment of the present invention.

Next, the structure of a microneedle array mounting jig 51 is explained with reference to FIG. 9. The microneedle array mounting jig 51 is made of metal, formed from a plate material by press working. First, there is a bottom plate 53, and two pairs of side walls 55, 55 are bent to be formed, respectively, on both the left and right surfaces of the bottom plate 53.

With regard to the side walls 55, 55 on one side, inclined guide grooves 57, 57 are provided, respectively. The inclined guide groove 57 is composed of a lower inclined guide wing 59 provided on the lower side, and an upper inclined guide wing 61 provided on the upper side. The upper inclined guide wing 61 is provided in the form of flat spring, with having an engagement projection 63. The tip surface of the engagement projection 63 serves as an inclined guide surface 65.

Note that, each of the all side walls 55, namely two on the both left and right sides, in total four, has the inclined guide groove 57 likewise.

Thus, the engagement projection 63 of the upper inclined guide wing 61 of the each of the inclined guide groove 57 is engaged with the engagement recess 23 of the liquid medicine feeding port side case 3 of the microneedle array 1 as explained above.

The bottom wall 53 has a plurality of (in the present embodiment, 6 holes×6 arrays=36 holes) penetration holes 71 perforated therethrough. The tip parts of the microneedles 37 as explained above penetrate through the plurality of penetration holes 71, respectively.

The microneedle array mounting jig 51 is provided with an adhesion part 81 by applying adhesive thereto, and a removable peel-off paper 83 is adhered to the surface thereof.

The function will be explained based on the structure as described above.

Figure 10:
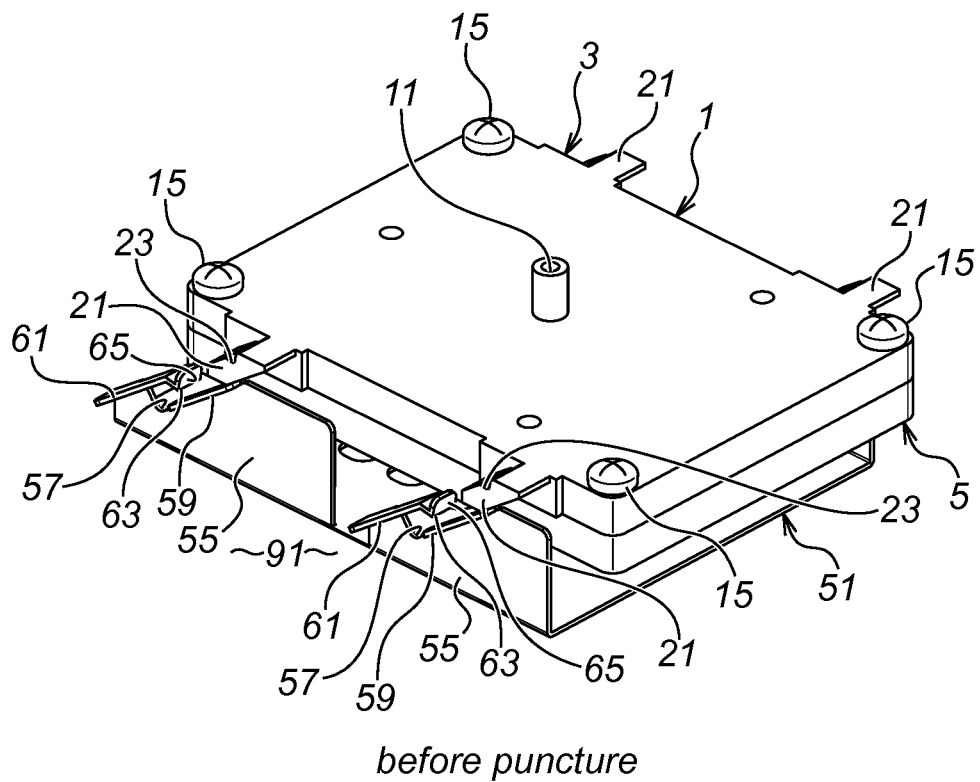
FIG. 10 A perspective view showing a state before puncture, in which the microneedle array is mounted on the microneedle array mounting jig according to the first embodiment of the present invention.

First, as illustrated in FIG. 10, the peel-off paper 83 is removed from the microneedle array mounting jig 51, so that the exposed adhesion part 81 adheres to be fixed on a skin 91.

Figure 11:
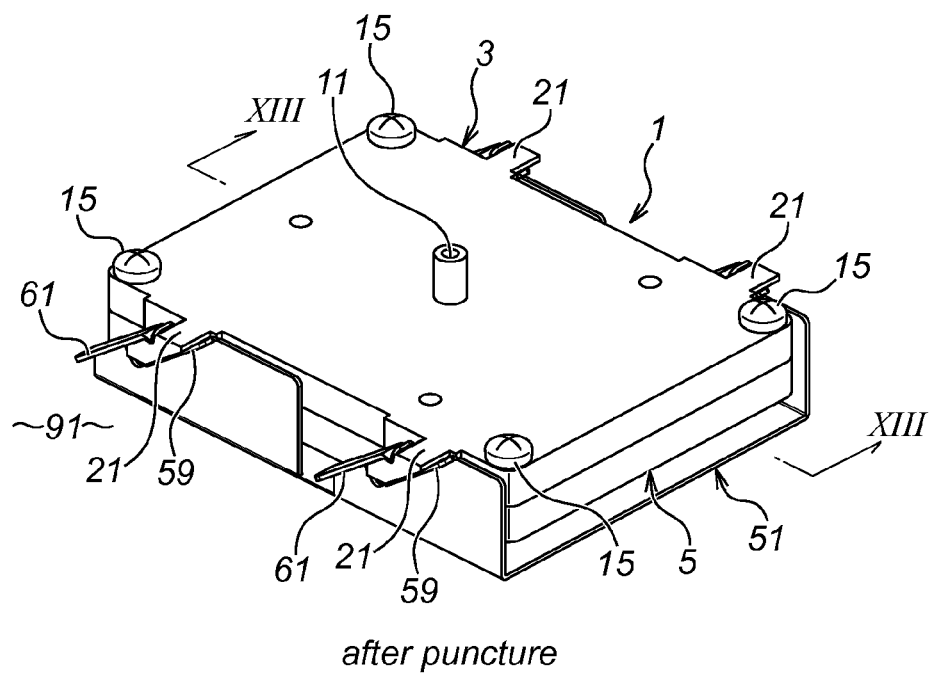
FIG. 11 A perspective view showing a state after puncture, in which the microneedle array is mounted on the microneedle array mounting jig according to the first embodiment of the present invention.
Figure 12:
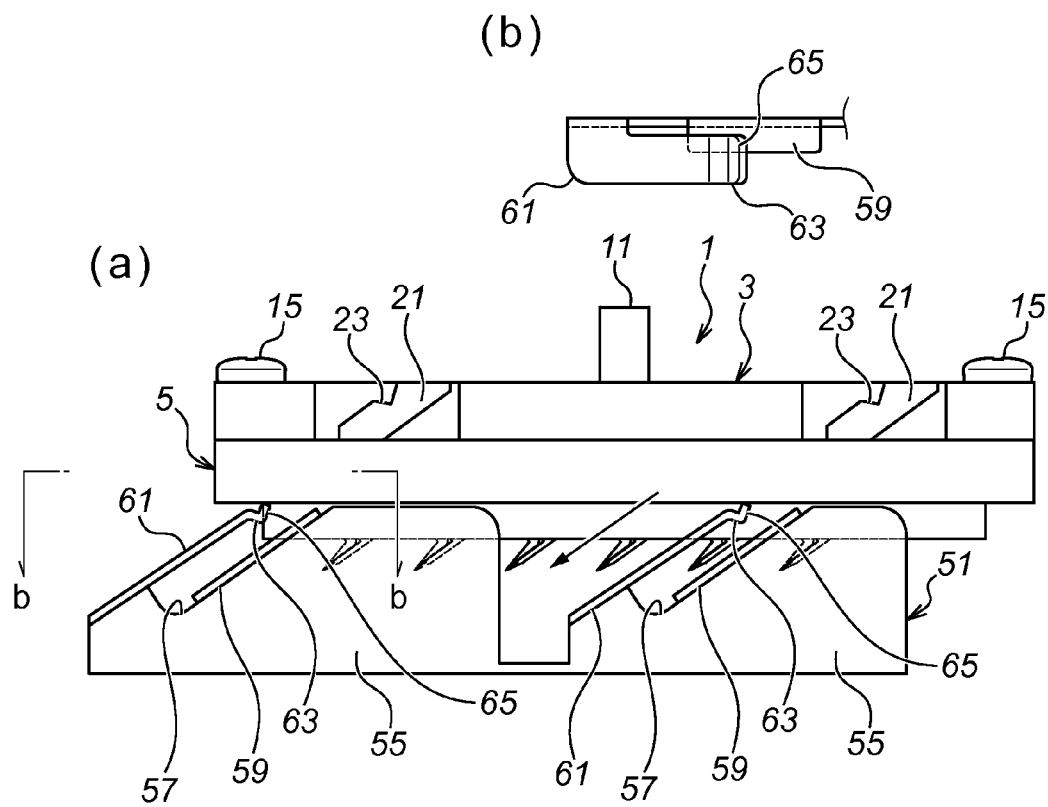
Figure 13:
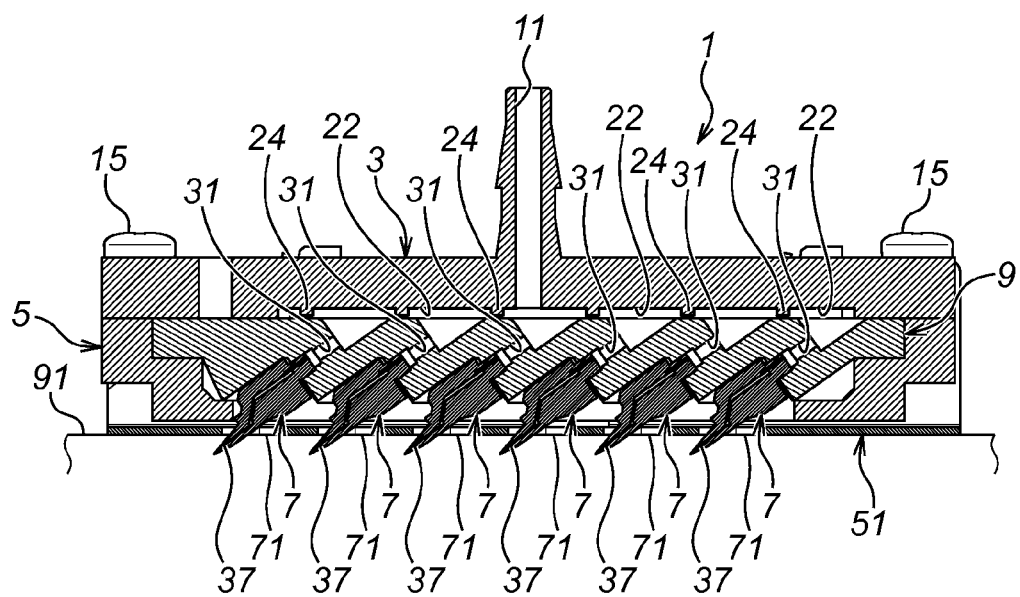
FIG. 13 A sectional view as seen from the line XIII-XIII of FIG. 11, according to the first embodiment of the present invention.

Next, as illustrated in FIG. 10, the microneedle array 1 is mounted on the microneedle array mounting jig 51 adhering to be fixed on the skin 91. And as illustrated in FIG. 11, the microneedle array 1 is mounted to be fixed to the microneedle array mounting jig 51, and further, is pressed against the skin 91 in an inclined state along the inclined guide grooves 57. Accordingly, a desired puncture can be performed. Thereafter, with the engagement of the engagement projections 63, 63 of the microneedle array mounting jig 51 with the in-use-state engagement recesses 23, 23 of the microneedle array 1, the microneedle array 1 is fixed to the microneedle array mounting jig 51.

Thus, a liquid medicine is fed from the liquid medicine feeding port 11, and flows into each of the liquid medicine channels 45 of each of the microneedle units 7 via the liquid medicine distribution grooves 22, and is injected under the skin, from each of the liquid medicine discharge ports 38 at the tip of the microneedle 37.

The present embodiment as described above has the following effects.

First, the microneedles 37 of the microneedle units 7 of the microneedle array 1 can be needled easily into the skin 91 in the inclined state. Accordingly, the liquid medicine can be surely injected under the skin, and moreover, the leakage of the liquid medicine can be prevented.

Moreover, the structure of the microneedle array mounting jig 51 is pressed against the skin 91, and therefore, it is possible to maintain the flat surface state of the skin 91. In particular, in the present embodiment, since the adhesion part 81 is provided on the surface of the microneedle array mounting jig 51, the effect of maintaining the flat surface state of the skin 91 can be exerted more surely. As described above, since the flat surface state of the skin 91 can be maintained, the deformation of the skin 91 during puncture can be prevented, and therefore, the microneedles 37 can be surely needled into a desired depth under the skin.

Moreover, since the microneedle array mounting jig 51 is provided with the inclined guide grooves 57, the microneedle array 1 can be mounted surely and easily, to the microneedle array mounting jig 51.

Moreover, the microneedle array mounting jig 51 is provided with the four engagement projections 63, and these four engagement projections 63 are engaged, respectively, with the in-use-state engagement recesses 23 of the liquid medicine feeding port side case 3 of the microneedle array 1, and therefore, the microneedle array 1 can be surely fixed to the microneedle array mounting jig 51, and the position of the microneedle array 1 against the skin 91 can also be surely fixed.

Next, a second embodiment of the present invention will be explained with reference to FIG. 16 to FIG. 19. In the second embodiment, with regard to the engagement projection 21 of the liquid medicine feeding port side case 3 of the microneedle array 1 in the first embodiment, apart from the in-use-state engagement recess 23, a non-use-state engagement recess 23' is provided.

Note that, the other structure is substantially the same as that of the first embodiment described above, and therefore the same reference signs are allotted to the same elements in the drawings, and the explain thereof will not be made.

Figure 18:
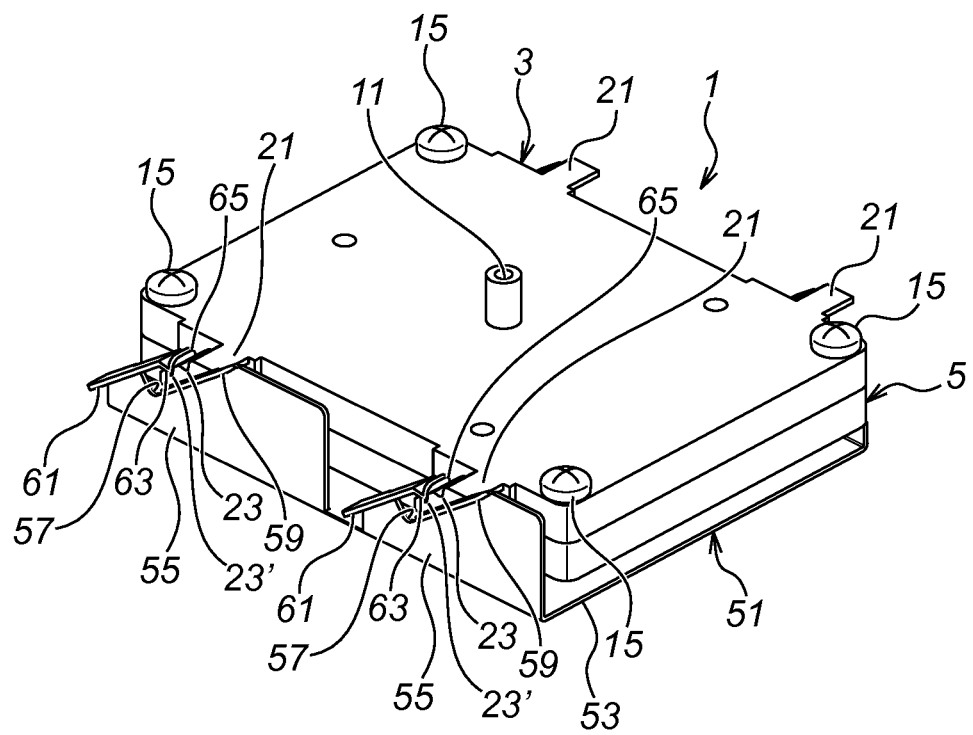
FIG. 18 A perspective view of the microneedle array device during non-use state, according to the second embodiment of the present invention.
Figure 19:
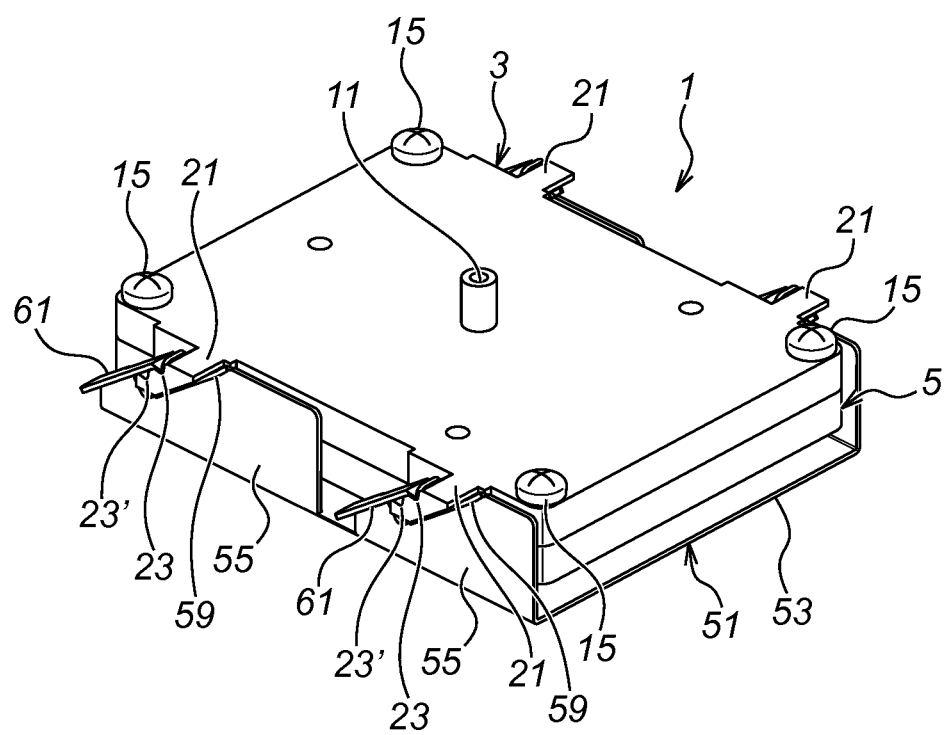
FIG. 19 A perspective view of the microneedle array device during in-use state, according to the second embodiment of the present invention.
Figure 20:
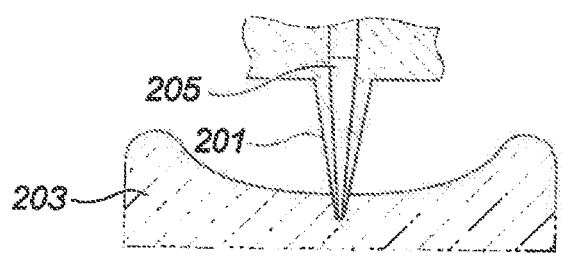
FIG. 20 A sectional view showing a state that a microneedle is pierced perpendicularly into a skin surface according to a prior art.

According to the above structure, during non-use state, as illustrated in FIG. 18, the non-use-state engagement recesses 23' of the engagement projections 21 are engaged with the engagement projections 63 of the upper inclined guide wings 61, respectively. In this state, the microneedles 37 of the microneedle array 1 will not protrude from the penetration holes 71 of the microneedle array mounting jig 51, and therefore, the microneedles 37 can be kept from any unintended damage thereto or any unintended puncture thereby.

Figure 17:
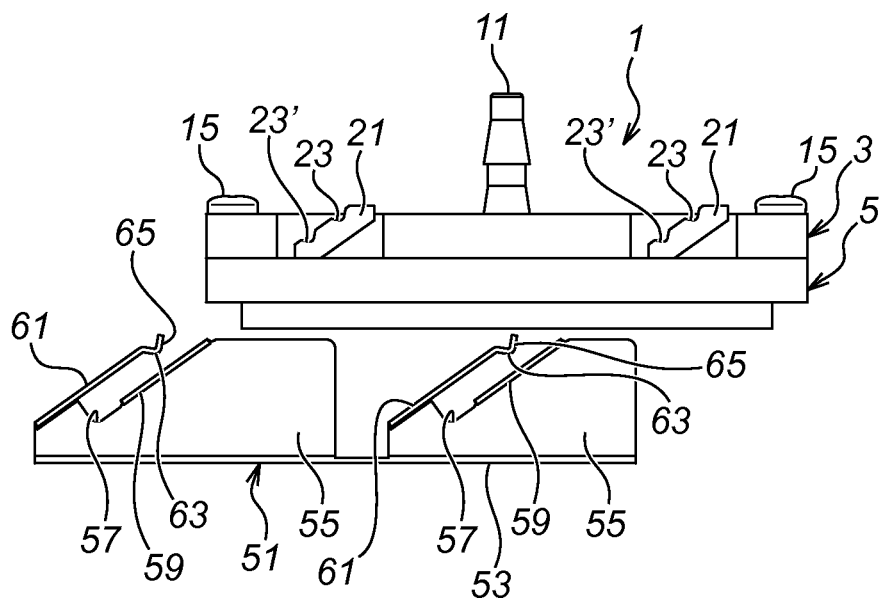
FIG. 17 An exploded perspective view of a microneedle array device according to the second embodiment of the present invention.

Thus, during in-use state, as illustrated in FIG. 17, and as already explained in the first embodiment, the in-use-state engagement recesses 23 of the engagement projections 21 are engaged with the engagement projections 63 of the upper inclined guide wings 61, respectively.

As described above, according to the second embodiment, the same effects as those of the first embodiment can be exerted, and in addition, during non-use state, the microneedles 37 can be kept from any unintended damage thereto or any unintended puncture thereby.

Note that, the present invention is not limited to the first and second embodiment as described above. For example, in the case of the first and second embodiments, the adhesion part is provided, but the present invention is not limited to this structure. For example, when the injection time is short, any structure without adhesion part can be provided.

For example, the number of microneedles, and the number of the corresponding penetration holes of the jig main body, can be determined arbitrarily.

Moreover, the shape of the microneedle is not also limited to the quadrangular pyramid shape, and various shapes, such as multangular pyramid shape or conical shape, can be used.

Moreover, instead of providing the adhesion part on the whole surface of the jig main body likewise the cases of the first and second embodiments, it is also possible to provide partially, such as the adhesion parts covering the openings of the penetration holes.

Moreover, in the first and second embodiments, the adhesion part is provided by applying the adhesive thereto, but it is also possible, for example, to be adhered by removing the peel-off paper on one side of the double-sided adhesive paper.

Moreover, in the first and second embodiments, the case is fastened by the screws, but it is also possible to be fastened by any versatile adhesion methods, such as adhesion by adhesive, or adhesion by heat welding.

Moreover, in the first and second embodiments, after the puncture is performed in inclined state, the liquid medicine is injected into the skin from liquid medicine injecting holes, but it is also possible to perform puncture in the inclined state, with the state that the surfaces of the microneedles have been coated with the liquid medicine in advance.

Moreover, in the examples of the first and second embodiments, the microneedle is composed with two divided elements, so that, by joining these two divided elements, the microneedle with flow channel formed therebetween can be obtained, but the present invention is not limited to this structure.

For example, it is also possible that, during or after molding, the two divided elements are slid to each other, so as to to form the flow channel therebetween.

Moreover, it is also possible to prepare the microneedle provided with the flow channels on the both sides by injection molding, and the flow channels on the both sides are communicated with each other by laser irradiation, whereby the microneedle provided with the flow channel can be obtained (Official Gazette of JP 2012-157406A).

Moreover, the microneedle is not limited to that composed of two divided elements, and it is also possible to be made of a single component. In this case, a hollow part serving as the flow channel may be formed during molding of a single microneedle, or a hole serving as the flow channel may be perforated by machining or laser processing after molding.

Further, the structures of the drawings are illustrated merely as the examples, and the present invention is not limited thereto.

INDUSTRIAL APPLICABILITY

The present invention relates to a microneedle array incorporating, for example, a plurality of microneedles in a case, and a microneedle array device using such a microneedle array, and more specifically, relates to those in which the microneedles are mounted in an inclined state with an angle against a surface of the case, so that, during injection with the microneedles, a pain of a patient can be relieved, and leakage of a liquid medicine can be prevented. For example, the present invention is suitable as the microneedle array and the microneedle array device used for transdermal administration of insulin, etc.

EXPLANATION OF REFERENCE NUMERALS AND SIGNS

1 Microneedle Array
3 Liquid Medicine Feeding Port Side Case (a part of a case as a microneedle unit support member)
5 Opening Side Case (a part of the case as the microneedle unit support member)
7 Microneedle
9 Needle Holder
11 Liquid Medicine Feeding Port
23 In-use-state Engagement Recess (engaged part)
23' Non-use-state Engagement Recess (engaged part)
27 Inclined Guide Groove
31 Inclined Guide Hole
33 Main-needle Side Divided Element
35 Sub-needle Side Divided Element
37 Microneedle
39 Channel Boss
51 Microneedle Array Mounting Jig
53 Bottom Plate
55 Side Wall
57 Inclined Guide Groove
65 Engagement Recess (engaging part)
71 Penetration Hole

The invention claimed is:

1. A microneedle array comprising:
   a case which includes:
      a liquid medicine feeding port; and
      an opening;
   a needle holder, detachably incorporated with the case, which includes inclined guide holes communicating with the liquid medicine feeding port and comprising an elastic material; and
   microneedle units, respectively having microneedles, including a liquid medicine channel having a position that is regulated by insertion into the inclined guide holes of the needle holder so that the liquid medicine feeding port, the inclined guide holes, and the liquid medicine channel are communicating with each other, and whereby tips of the microneedles are held by the needle holder in an inclined state protrusively disposed from the opening of the case,
   wherein, feeding of a liquid medicine, having been fed via the liquid medicine feeding port, is performed via the inclined guide holes and the liquid medicine channel of the microneedles.

2. The microneedle array as claimed in claim 1, wherein, the microneedle units are provided with channel bosses that insert into the inclined guide holes to hold the microneedle units in the inclined state.

3. The microneedle array as claimed in claim 2, wherein the needle holder holds a plurality of rows of the microneedle units. holes to hold the microneedle units in the inclined state.

4. The microneedle array as claimed in claim 1, wherein, the microneedle units comprise a bonding structure of two divided elements, and the liquid medicine channel is formed between the two divided elements.

5. The microneedle array as claimed in claim 4, wherein the tips of the microneedles are formed only by one of the two divided elements.

6. A microneedle array device, comprising:
   the microneedle array as claimed in claim 1; and
   a microneedle array mounting jig for guiding the microneedle array in an inclined direction.

7. The microneedle array device as claimed in claim 6, wherein,
   the microneedle array mounting jig includes:
      a jig main body including penetration holes for passing the microneedles of the microneedle array therethrough; and
      guide parts for guiding the microneedle array incorporated in the jig main body in the inclined direction, so that the microneedles are introduced to the penetration holes.

8. The microneedle array device as claimed in claim 7, wherein,
   a surface of the jig main body provided with the penetration holes, includes an adhesion part.

9. The microneedle array as claimed in claim 8, wherein a peel-off paper is adhered to the adhesion part during a non-use state, and during an in-use state, with peeling off of the peel-off paper, the adhesion part is exposed.

10. The microneedle array device as claimed in claim 7, wherein,
    the jig main body includes a microneedle array holder for holding the incorporated microneedle array.

11. The microneedle array device as claimed in claim 10, wherein, the microneedle array holder includes engaging projection parts provided on side surfaces of the jig main body, and the microneedle array is held by engagement of the engaging projection parts with engaged recess parts provided on the microneedle array.

12. The microneedle array device as claimed in claim 11, wherein,
each of the engaged recess parts includes a non-use-state engaged recess part and an in-use-state engaged recess part, so that the non-use-state engaged recess part is engaged with one of the engaging projection parts of the jig main body during a non-use state so as to prevent unintended puncture of the microneedles, and the in-use-state engaged recess part is engaged with the one of the engaging projection parts of the jig main body during an in-use state so as to maintain a puncture state of the microneedle array.

13. The microneedle array as claimed in claim 1, wherein the inclined guide holes are inclined with respect to a plane of which the microneedles obliquely pierce.

14. The microneedle array as claimed in claim 1 wherein the tips are exposed from the case.

\* \* \* \* \*